United States Patent [19]
Domke et al.

[11] Patent Number: 5,587,147
[45] Date of Patent: *Dec. 24, 1996

[54] AQUEOUS ZINC-POLYAMIDE COMPLEX SOLUTION

[75] Inventors: Todd W. Domke, Newtown, Pa.; Wolfgang R. Bergmann, Princeton, N.J.

[73] Assignee: Church & Dwight Co., Inc., Princeton, N.J.

[*] Notice: The portion of the term of this patent subsequent to Jun. 30, 2014, has been disclaimed.

[21] Appl. No.: 269,155

[22] Filed: Jun. 30, 1994

[51] Int. Cl.$^6$ .............................. A61K 7/16; A61K 7/22
[52] U.S. Cl. ................................. 424/54; 424/49
[58] Field of Search ........................... 424/49–58

[56] References Cited

U.S. PATENT DOCUMENTS

| | | | |
|---|---|---|---|
| 3,862,308 | 1/1975 | Schmitt et al. | 424/54 |
| 4,020,019 | 4/1977 | Soldati et al. | 260/2 |
| 4,022,880 | 5/1977 | Vinson et al. | 424/49 |
| 4,082,841 | 4/1978 | Pader | 424/50 |
| 4,146,607 | 3/1979 | Ritchey | 424/54 |
| 4,396,599 | 8/1983 | Sipos | 424/52 |
| 4,428,930 | 1/1984 | Chang | 424/52 |
| 4,522,806 | 6/1985 | Muhlemann et al. | 424/52 |
| 4,568,540 | 2/1986 | Asano et al. | 424/52 |
| 4,575,457 | 3/1986 | Mazarin | 424/52 |
| 4,891,211 | 1/1990 | Winston | 424/52 |
| 4,971,782 | 11/1990 | Rudy et al. | 424/53 |
| 5,215,740 | 1/1993 | Domke et al. | 424/52 |
| 5,330,748 | 1/1994 | Winston et al. | 424/49 |
| 5,372,802 | 12/1994 | Barrons et al. | 424/52 |
| 5,374,368 | 12/1994 | Hauschild | 252/95 |
| 5,385,727 | 1/1995 | Winston et al. | 424/49 |
| 5,424,060 | 6/1995 | Hauschild | 424/52 |
| 5,455,024 | 10/1995 | Winston et al. | 424/52 |
| 5,456,902 | 10/1995 | Williams et al. | 424/49 |

OTHER PUBLICATIONS

Schmitt C–A. 78:20134 of Ger DE 2216242 (Oct. 12, 1972).
Beggs et al. C–A. 116:11234 of E.P. 451972 (Oct. 16, 1991).
Aleksina C–A. 106:219595 of USSR 1251906 (Aug. 23, 1986).
Muehleman C–A. 97:60838 of EP. 49830 (Apr. 21, 1982).

*Primary Examiner*—Shep K. Rose
*Attorney, Agent, or Firm*—Irving Fishman

[57] ABSTRACT

This invention provides a single-phase aqueous solution of a zinc-polyamine complex which is stable and has a clear transparency. The aqueous solution can be incorporated as a component of an oral care product such as a mouthwash or toothpaste. The zinc-polyamine complex enhances the control of oral malodor, plaque, calculus and gingivitis in dental applications, and decreases the astringency and metallic taste which is characteristic of zinc ions in an oral cavity.

6 Claims, 1 Drawing Sheet

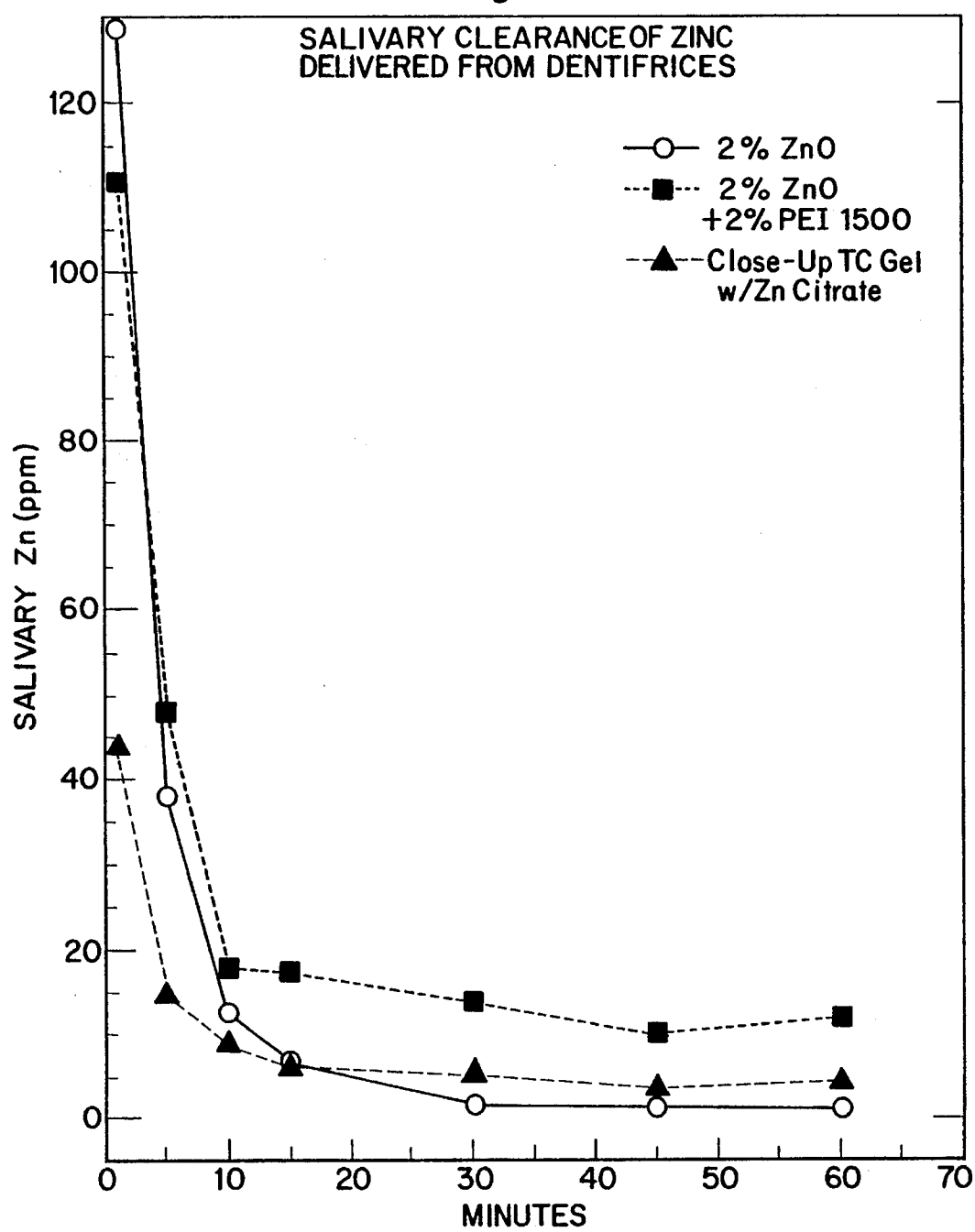

5,587,147

AQUEOUS ZINC-POLYAMIDE COMPLEX SOLUTION

BACKGROUND OF THE INVENTION

The use of zinc compounds as a source for physiologically active zinc ions in oral care products such as mouthwashes, rinses and toothpastes is a widely accepted practice. Zinc has been used for its ability to neutralize oral malodor, and it is also recognized that zinc ions have antiplaque and anticalculus properties.

It is hypothesized that the mechanism of zinc ions in reducing calculus in dental applications is interference with two stages in the development of calculus, i.e., the structural formation of the plaque stage, and the mineralization of the plaque stage. Both of these stages normally make the plaque more cohesive, and therefore less permeable to penetration by the physiologically active chemical species in the oral environment. Zinc interferes with the attachment of the microbial elements to each other and to the mucilaginous matrix, and also can interfere with the calcification stage. In both stages the zinc ions function as an antagonist to calcium ions. It is postulated that a zinc compound, by preventing the plaque from becoming dense and strongly cohesive, causes permeability in the plaque which allows penetration by the physiologically active antiplaque and anticalculus ions in the oral environment.

Both water-soluble and water-insoluble zinc compounds have been utilized as physiologically active ingredients in oral care preparations. Water-soluble and highly ionized zinc compounds such as zinc chloride provide the best source of bioavailable zinc ions. However, zinc chloride in aqueous solution tends to form oxychlorides and zinc hydroxides of low solubility, which results in a two-phase cloudy solution.

The pH of a conventional zinc chloride solution can be lowered to less than 4.5 through the use of mineral or organic acid buffers to provide a stable and clear solution. However, this method is not acceptable since the resultant oral care product exhibits severe astringency and an undesirable metallic taste.

Zinc salts such as zinc phenolsulfonate as disclosed in U.S. Pat. No. 4,022,880, and zinc carboxymethylsuccinate, as disclosed in U.S. Pat. No. 4,144,323, tend to be stable at a higher pH than other zinc salts. Sparingly water-soluble salts such as zinc citrate have been used to moderate the release of zinc ions, thereby reducing astringency and providing a sustained level of in-vivo anticalculus activity. The use of various complexing agents such as sodium gluconate (U.S. Pat. No. 4,568,540), glycine (U.S. Pat. No. 4,339,432 and U.S. Pat. No. 4,425,325), sodium citrate, citric acid, and the like, have been employed for production of relatively stable solutions of zinc chloride.

The reaction or interaction of zinc compounds of varying solubility with anionic polymers containing carboxylic, sulfonic and/or phosphonic acid functionalities are described in U.S. Pat. No. 4,138,477.

U.S. Pat. No. 4,664,906 describes oral compositions containing hexidine and a zinc compound which exhibit antimicrobial activity. Opacified gel dentifrices are disclosed with contain sodium gluconate and a nonionic binder such as hydroxyethylcellulose.

U.S. Pat. No. 4,992,259 describes a clear aqueous composition of a zinc salt, a complexing agent such as succinic acid, and an anionic polymer such as sodium alginate.

Prior art of particular interest with respect to the present invention subject matter includes U.S. Pat. Nos. 4,022,880; 4,082,841; and 4,522,806. These references describe oral care products which contain a zinc compound and a polyamine compound as two of the formulation ingredients.

There is continuing interest in the development of new and improved oral care products which retard plaque and calculus formation in oral cavities.

Accordingly, it is an object of this invention to provide an oral care product which has superior properties for controlling oral malodor, plaque, calculus and gingivitis.

It is another object of this invention to provide an ingredient for oral care compositions which slow-releases bioavailable zinc ions in an oral cavity environment.

It is a further object of this invention to provide a clear single-phase aqueous solution of a normally water-insoluble zinc compound which has utility as an ingredient of improved palatability and reduced astringency in oral care compositions.

Other objects and advantages of the present invention shall become apparent from the accompanying description and examples.

FIG. 1 is a graph which represents the mean salivary zinc concentration vs. time curves for three dentifrices. The graph comparative data have correspondence with the dentifrice formulations and procedures described in Example V.

DESCRIPTION OF THE INVENTION

One or more objects of the present invention are accomplished by the provision of a single-phase aqueous solution comprising (1) about 0.1–12 weight percent of water-insoluble zinc compound ingredient; and (2) about 0.1–10 weight percent of water-soluble zinc-complexing polyamine ingredient; wherein the aqueous solution has a pH in the range between about 6–10.

The term "single-phase" as employed herein refers to an invention aqueous solution which has a clear transparency, without any visible evidence of a second phase which is distinct from the aqueous phase.

The term "water-insoluble" as employed herein refers to a zinc-containing compound which normally has a solubility in water that is equivalent to less than about one gram of zinc ions in 100 milliliters of water at 25° C. The slight solubility of the zinc compound in water is sufficient to slow-release bioavailable zinc ions in an oral environment.

The term "water-soluble" as employed herein refers to polyamines which have a solubility of at least about two grams per 100 milliliters of water at 25° C.

Zinc compounds having a solubility which provides less than about one gram of bioavailable zinc ions per 100 milliliters of water at 25° C., and which are suitable as an ingredient in an invention aqueous solution, include zinc oxide, zinc silicate, zinc carbonate, zinc stannate, zinc tetrafluoroborate, zinc hexafluorosilicate, zinc citrate, zinc benzoate, and the like.

Polyamines which are suitable as an ingredient in an invention aqueous solution include water-soluble chemical structures such as polyalkylenamines having a weight average molecular weight between about 800–1,000,000. A preferred type of polyalkylenamine is one which corresponds to the formula:

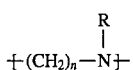

where R is a $C_1$–$C_3$ alkyl substituent, and n is an integer in the range of 2–6.

A polyamine ingredient can contain other heteroatoms such as oxygen and sulfur. The amine groups can be any combination selected from primary, secondary and tertiary amine structures. The polyamine ingredient must have sufficient amine basicity to coordinate with the zinc compound and form a water-soluble zinc-polyamine complex.

Another type of polyamine which can be employed as a zinc-complexing ingredient in an invention aqueous solution is a basic aminoacid polymer having a weight average molecular weight between about 1500–70,000. Illustrative of these aminoacid polymers are polyarginine, polylysine and polyhistidine.

A present invention aqueous solution can be prepared by dissolving the polyamine ingredient in the aqueous medium, and then adding the zinc compound in powder form to the aqueous solution with stirring. The dissolution rate of the zinc compound can be accelerated by mild heating at a temperature between about 30°–60° C.

Solubilizing of the zinc compound in the aqueous solution also can be facilitated by employing an ultrafine powder form. Zinc oxide having an average particle size less than about five microns is a commercially available product.

After completion of the zinc compound addition, the resultant clear aqueous solution can have a pH above about 10 because of the polyamine basicity. Preferably, an acid reagent such as hydrochloric acid is added to adjust the aqueous solution pH into the range between about 6–10.

A pH above about 10 can have an irritating effect on sensitive membranes when the aqueous solution is used in a dental application. A pH below about 6 can cause a demineralization of the tooth enamel. It is advantageous to maintain the aqueous solution pH in the 6–10 range.

A present invention aqueous solution can be incorporated as a component of oral care products such as mouthwashes and toothpastes. The oral care products can be formulated to provide a zinc ion concentration between about 0.05–4 weight percent. A typical oral care product will have a zinc ion concentration between about 0.2–2.0 weight percent.

A present invention aqueous solution can be formed into a toothpaste by blending the formulation with dentifrice ingredients, such as sodium bicarbonate, flavorant, sweetener, and the like.

Suitable flavorants include oils of spearmint, peppermint, wintergreen, sassafras, clove, sage, eucalyptus, marjoram and cinnamon, and flavorants such as methyl salicylate and menthol.

Suitable sweeteners include sodium saccharin, sodium cyclamate, xylitol, perillartine, D-tryptophan, aspartame, and the like.

By the practice of the present invention, an oral care product can be prepared which has superior properties for combatting bad breath and periodontal disease, and retarding plaque and calculus formation. Important advantages derive from the presence of a present invention zinc-polyamine complex as a component of an oral care product.

A present invention zinc-polyamine complex can be adsorbed onto oral surfaces. The zinc-polyamine complex provides a means of attachment in the oral cavity, and functions as a reservoir of zinc ions which are sustained-released over an extended time period and are effective for combatting mouth odor, periodontal disease, plaque and calculus.

As a further advantage, the zinc-polyamine complex is in a form that decreases the astringency and metallic taste which is characteristic of zinc ions, and thereby leaves a more pleasant taste in the mouth.

The following examples are further illustrative of the present invention. The components and specific ingredients are presented as being typical, and various modifications can be derived in view of the foregoing disclosure within the scope of the invention.

EXAMPLE I

This Example illustrates the preparation of a present invention aqueous solution containing a zinc-polyamine complex.

| Ingredients | Parts By Weight |
| --- | --- |
| Polymin P[1] | 12 |
| hydrochloric acid (50% aq. sol.) | 21 |
| zinc oxide powder | 4 |
| distilled water | to 100 |

[1]PEI 1500 (CTFA); polyethylenimine (M.W. 75,000; BASF)

The polyamine is dissolved in about 50 parts of distilled water. The zinc oxide powder is added to the aqueous solution, and stirring is continued for about 30 minutes. Hydrochloric acid solution is added to adjust the pH to 7–8. Distilled water is added to 100 parts by weight.

The final aqueous solution is a single phase transparent medium with a pH of 7–8.

A similar solution of zinc-polyamine complex is obtained when zinc citrate is employed instead of zinc oxide.

EXAMPLE II

This Example illustrates comparative data which demonstrate that a present invention aqueous solution of zinc compound and polyamine exhibits an enhanced anticalculus effect.

Anticalculus evaluation is conducted with an in-vitro method similar to that described in J. Clin. Den., 2, 48 (1990) by Schiff & Volpe. A higher T1 value represents a greater anticalculus effect.

| Aqueous Systems | T1, minutes |
| --- | --- |
| 1. Water control | 14.25 |
| 2. 2% zinc oxide aqueous suspension | 15.00 |
| 3. 6% PEI[1] | 14.25 |

-continued

| Aqueous Systems | T1, minutes |
| --- | --- |
| 4. 0.25% PEI + 2.0% zinc oxide | 16.00 |
| 5. 0.25% PEI + 4.0% zinc oxide | 16.00 |
| 6. 2.0% PEI + 2.0% zinc oxide | 21.00 |
| 7. 2.0% PEI + 4.0% zinc oxide | 21.50 |
| 8. 5.0% TSPP[(2)] aqueous solution | 23.00 |
| 9. Cogate TC | 20.00 |
| 10. 6% PEI + 2% zinc oxide | 26.50 |
| 11. Crest TC | 27.75 |
| 12. 5.0% zinc citrate[(3)] | 17.25 |
| 13. 5.0% zinc citrate + 2% PEI | 25.75 |
| 14. 2.0% PEI + 4.0% zinc oxide + 2.0% TSPP | 32.00 |
| 15. 6.0% PEI + 2.0% zinc oxide + 5.0% TSPP | 50.25 |

[(1)]polyethylenimine (M.W.; BASF).
[(2)]tetrasodium pyrophosphate.
[(3)]2% zinc oxide and 5% zinc citrate are equivalent in zinc molarity.

EXAMPLE III

This Example illustrates the preparation of a dentifrice composition which contains an aqueous solution of a zinc-polyamine complex in accordance with the present invention.

A pre-blend is prepared with the following ingredients:

| | Parts By Weight |
| --- | --- |
| Polyethylene glycol (M.W. 400) | 1.00 |
| Glycerin | 14.00 |
| Sodium carboxymethylcellulose | 0.90 |
| Sodium fluoride | 0.24 |
| Distilled water | 10.91 |

The pre-blend is admixed with additional ingredients to form a composition with a toothpaste consistency:

| | Weight Percent |
| --- | --- |
| Zinc oxide-PEI solution (Example I) | 15.00 |
| Sodium bicarbonate | 55.00 |
| Sodium lauryl sulfate | 0.30 |
| Sodium lauroyl sarcosinate | 1.00 |
| Flavor | 0.75 |
| Saccharin | 0.90 |

EXAMPLE IV

This Example illustrates the preparation of a mouthwash formulation which contains an aqueous solution of a zinc-polyamine complex in accordance with the present invention.

A formulation is prepared from the following ingredients:

| | Parts By Weight |
| --- | --- |
| Ethanol (5% water) | 10.00 |
| Propylene glycol | 5.00 |
| Xanthan gum | 0.03 |
| Sodium lauryl sulfate | 0.30 |
| Zinc citrate-PEI solution[(1)] | 20.00 |
| Benzethonium chloride | 0.01 |
| Sodium saccharin | 0.10 |
| FDC Red 40 (1% solution) | 0.80 |
| 4483T flavorant (Carruba Inc.) | 0.30 |
| 10% by weight aqueous sodium bicarbonate | 40.00 |
| Water | to 100 |

[(1)]2% zinc citrate:2% polyethylenimine aqueous solution prepared by the method of Example I.

A solution is formed of the ethanol, propylene glycol, zinc citrate-PEI solution and water. The xanthan gum is added, followed by the other ingredients in the listed order with high speed stirring. The sodium bicarbonate is added to the liquid mixture as a warm solution (40° C.).

EXAMPLE V

This Example illustrates the increased oral retention of zinc with a toothpaste dentifrice which contains zinc compound and polyamine ingredients in accordance with the present invention.

Comparative salivary tests are conducted to determine the effect of polyethyleneimine on the salivary clearance of zinc oxide delivered from a sodium bicarbonate-containing dentifrice.

Dentifrices containing 59.25% sodium bicarbonate and 2% zinc oxide with and without 2% polyethyleneimine are prepared, with complete formulations as shown in Table 1. A commercial dentifrice containing 2% zinc citrate trihydrate (ZnCit) also is tested (Close-Up Tartar Control Gel).

The three zinc-containing dentifrice products are tested in a blind cross-over brushing design. Six human subjects are recruited, and they abstain from all oral hygiene on the morning of each test. Only one product per day is tested, and the subjects are blinded to the identity of the products. On the day of testing, an unstimulated saliva sample is obtained from each subject prior to brushing. The subjects brush with 2 g of a test product for 60 seconds and rinse for 5 seconds with 15 ml of distilled water. Following rinsing, unstimulated saliva samples are collected at 1, 5, 10, 15, 30, 45 and 60 minutes. During this period the subjects refrain from eating, drinking or gum chewing, and minimize talking. After sample collection, 0.4 ml of each saliva sample is diluted with 5 ml 1N HCl in polypropylene vials. The diluted samples are mixed using a vortex mixer, and analyzed for zinc using ICP spectrophotometry.

The mean salivary zinc concentration vs. time curves for the three test dentifrices are shown in FIG. 1. Prior to brushing, the mean baseline salivary zinc concentrations are 0.56, 0.41 and 0.59 μg Zn/ml saliva for the ZnO, ZnO/PEI 1500 and commercial zinc citrate dentifrices (ZnCit), respectively. The salivary clearance curves for the test products exhibit a typical biphasic salivary clearance pattern. This is characterized by a rapid initial decline in salivary zinc followed by a slower secondary elimination of zinc from saliva.

The salivary zinc levels for all dentifrice products as expected is highest immediately following the water rinse. At 1 minute post-brushing, the mean salivary zinc concentrations are 111, 129 and 44 μg Zn/ml for the ZnO, ZnO/PEI 1500 and ZnCit dentifrices, respectively. At 5 minutes, the mean salivary zinc levels are 39, 48 and 15 μg Zn/ml, respectively. Differences between products at 1 and 5 minutes post-brushing are due to differences in product zinc concentrations. The ZnCit dentifrice contains 2.0% zinc citrate trihydrate, which is equivalent to about 0.62% Zn or 0.78% ZnO. In comparison, the ZnO dentifrices contain 2.0% ZnO. While higher initial concentrations of zinc are obtained as a result of increased levels of zinc in the ZnO dentifrices, the effect is transitory and not sustained beyond 5 minutes post-brushing.

The mean salivary zinc levels at 10 minutes post-brushing decreased to 13, 18 and 9 μg Zn/ml respectively for the ZnO, ZnO/PEI and ZnCit dentifrices. These levels are not significantly different from each other (p>0.05). At 15 to 60 minutes post-brushing, the ZnO/PEI 1500 dentifrice provides significantly (p<0.05) higher mean salivary zinc levels then either the ZnO or ZnCit dentifrices. The ZnO/PEI 1500 dentifrice provides mean salivary zinc concentrations ranging between 10 to 18 μg Zn/ml during the 15 to 60 minutes post-brushing. In comparison, the ZnCit dentifrice provides mean salivary zinc concentrations ranging from 4 to 6 μg Zn/ml. Similarly, the mean salivary zinc concentration provided by the ZnO dentifrice drops from 7 μg Zn/ml at 15 minutes to less than 2 μg Zn/ml at 60 minutes. There are no differences between the ZnCit and the ZnO dentifrices during this time period. A statistical summary of the data is illustrated in Table 2.

The salivary test data indicate that zinc can be delivered at a high level to the oral cavity from a zinc oxide baking soda dentifrice, and that the addition of PEI 1500 significantly increases the oral retention of zinc. This delivery and retention directly relates to the beneficial bioactivity of zinc, since the bioactivity of an oral antimicrobial agent is dependent upon the delivery of an effective concentration, i.e., the dosage, frequency of application, and retention of the agent within the oral cavity.

During the saliva collection periods, five of the six subjects offer comments that the aftertaste of the commercial zinc citrate dentifrice is objectionable. The metallic aftertaste and high degree of astringency are the most prevalent observations. The metallic taste and astringent feeling of soluble and partially soluble zinc salts is well-known. The magnitude of these perceptions is dependent upon zinc concentration. Although the ZnO/PEI 1500 dentifrice provides a higher sustained level of salivary zinc, no subject finds this product to possess any objectional metallic or astringent aftertaste as is noted with the ZnCit product. The PEI 1500 appears to moderate the taste perception of zinc.

TABLE I

ZINC OXIDE DENTIFRICES WITH AND WITHOUT PEI 1500

| INGREDIENT | Parts By Weight | |
|---|---|---|
| | ZnO | ZnO/PEI |
| Zinc oxide | 2.000 | 2.000 |
| PEI 1500 (50% soln., Polymin P; BASF) | 0.000 | 4.000 |

TABLE I-continued

ZINC OXIDE DENTIFRICES WITH AND WITHOUT PEI 1500

| INGREDIENT | Parts By Weight | |
|---|---|---|
| | ZnO | ZnO/PEI |
| 50% HCl (6N HCl) | 0.000 | 3.500 |
| Distilled water | 19.173 | 11.673 |
| Sodium bicarbonate | 59.250 | 59.250 |
| Glycerin (99.7%) | 14.070 | 14.070 |
| PEG-8 (Carbowax 400; Union Carbide) | 1.000 | 1.000 |
| Sodium carboxymethyl-cellulose | 0.850 | 0.850 |
| Sodium fluoride | 0.243 | 0.243 |
| Sodium saccharin | 1.208 | 1.208 |
| Sodium lauryl sulfate | 0.300 | 0.300 |
| Hamposyl L-30 (Grace)[1] | 1.000 | 1.000 |
| Flavor (H&R 9377) | 0.906 | 0.906 |
| Total | 100.00 | 100.00 |

[1]Sodium lauroyl sarcosinate.

TABLE 2

STATISTICAL SUMMARY OF RESULTS*

| TEST PRODUCT | 1–5 mins. | 10 mins. | 15–60 mins. |
|---|---|---|---|
| ZnO/PEI dentifrice | A | B | |
| | A | B | |
| ZnO dentifrice | A | B | C |
| | | B | C |
| Close Up (Zn Citrate) | | B | C |

*Products with the same letter are not statistically different (p.0.05) within the specified time period.

What is claimed is:

1. A single-phase aqueous solution comprising (1) about 0.1–12 weight percent of water-insoluble zinc compound ingredient selected from the group consisting of zinc oxide, zinc silicate, zinc carbonate, zinc stannate, zinc tetrafluoroborate, zinc citrate, zinc benzoate and zinc hexafluorosilicate; and (2) about 0.1–10 weight percent of water-soluble zinc-complexing polyalkylenamine polyamine ingredient; wherein the aqueous solution has a pH in the range between about 6–10.

2. An aqueous solution in accordance with claim 1 wherein the zinc compound ingredient is zinc oxide.

3. An aqueous solution in accordance with claim 1 wherein the polyamine ingredient is polyalkylenamine having a molecular weight between about 800–1,000,000.

4. An aqueous solution in accordance with claim 1 wherein the polyamine ingredient is polyethyleneimine.

5. An aqueous solution in accordance with claim 1 which is incorporated in an effective anticalculus quantity as an ingredient in an oral care composition.

6. An aqueous solution in accordance with claim 5 wherein the oral care composition is a toothpaste formulation.

* * * * *